United States Patent [19]

Hoffmann et al.

[11] 4,296,241
[45] Oct. 20, 1981

[54] PREPARATION OF 3-(2,2-DICHLOROVINYL)-2,2-DIMETHYL-CYCLOPROPANE-1-CARBOXYLIC ACID DERIVATIVES

[75] Inventors: Hellmut Hoffmann; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 165,871

[22] Filed: Jul. 2, 1980

[30] Foreign Application Priority Data

Jul. 21, 1979 [DE] Fed. Rep. of Germany ....... 2929725
Mar. 11, 1980 [DE] Fed. Rep. of Germany ....... 3009242

[51] Int. Cl.$^3$ .................................................. C07C 69/743
[52] U.S. Cl. .................................... 560/124; 562/506
[58] Field of Search ......................... 560/124; 562/506

[56] References Cited

U.S. PATENT DOCUMENTS

4,024,163 5/1977 Elliott .............................. 560/506

FOREIGN PATENT DOCUMENTS

494525 9/1976 Australia ............................ 560/124
7142 1/1980 European Pat. Off. ............ 560/124
1446304 8/1976 United Kingdom ................ 560/124

OTHER PUBLICATIONS

Savignac, Synthesis, 8, pp. 535-536 (1975).
Zimmer, Chemia, 28, pp. 656-657 (1974).

*Primary Examiner*—Natalie Trousof
*Assistant Examiner*—Michael Shippen
*Attorney, Agent, or Firm*—Sprung, Felfe, Horn, Lynch & Kramer

[57] ABSTRACT

A process for the preparation of a 3-(2,2-dichlorovinyl)-2,2-dimethyl-cyclopropane-1-carboxylic acid or derivative of the formula

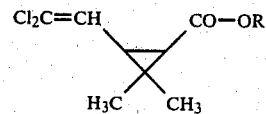

in which R is hydrogen, alkali metal, ammonium, an equivalent of an alkaline earth metal, alkyl, or a radical customary in the alcohol part of pyrethroids, comprising reacting a 3-formyl-2,2-dimethyl-cyclopropane-1-carboxylic acid derivative of the formula

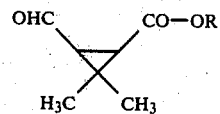

with a dichloromethane derivative of the formula

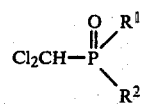

in which $R^1$ and $R^2$ each independently is alkyl, phenyl, alkoxy or phenoxy, or together are alkanediyl or alkanedioxy, in the presence of a base at a temperature between about $-50°$ and $+50°$ C. The products are intermediates for the preparation of esters of pyrethroid-like insecticidal activity.

9 Claims, No Drawings

PREPARATION OF 3-(2,2-DICHLOROVINYL)-2,2-DIMETHYL-CYCLOPROPANE-1-CARBOXYLIC ACID DERIVATIVES

The invention relates to an unobvious process for the preparation of certain known 3-(2,2-dichloro-vinyl)-2,2-dimethyl-cyclopropane-1-carboxylic acid derivatives.

It is known that 3-(2,2-dichloro-vinyl)-2,2-dimethyl-cyclopropane-1-carboxylic acid esters are obtained when 3-formyl-2,2-dimethyl-cyclopropane-1-carboxylic acid esters are reacted with triphenyl-phosphine in carbon tetrachloride (see DE-OS (German Published Specification) No. 2,326,077).

However, the desired products are obtained in only moderate yields by this synthesis method.

It is also known that 1,1-dichloro-alkanes are obtained when lithium salts of dichloromethane-phosphonic acid esters are reacted with aldehydes or ketones (see Synthesis 1975, 535–536).

However, the preparation of the lithium salts of dichloromethane-phosphonic acid esters is relatively troublesome: they are obtained from chloromethane-phosphonic acid esters by reaction with butyl-lithium and carbon tetrachloride at −75° C., it being necessary to use thoroughly dried solvents, and an inert gas atmosphere being required.

The present invention now provides a process for the preparation of a 3-(2,2-dichloro-vinyl)-2,2-dimethylcyclopropane-1-carboxylic acid derivative of the general formula

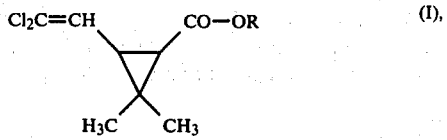

in which R represents hydrogen, alkali metal, ammonium, an equivalent of alkaline earth metal alkyl or a radical customary in the alcohol part of pyrethroids, in which a 3-formyl-2,2-dimethyl-cyclopropane-1-carboxylic acid derivative of the general formula

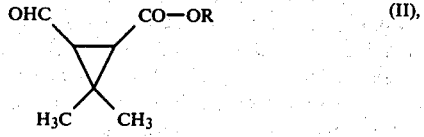

in which R has the meaning indicated above, is reacted with a dichloromethane derivative of the general formula

in which $R^1$ and $R^2$ individually represent alkyl, phenyl alkoxy or phenoxy or together represent alkanediyl (alkylene) or alkanedioxy (alkylenedioxy), in the presence of a base and if appropriate using a diluent, at a temperature between −50° and +50° C.

It is surprising that 3-(2,2-dichloro-vinyl)-2,2-dimethyl-cyclopropane-1-carboxylic acid derivatives are obtained in good yields in a considerably simpler and less expensive manner by the process according to the invention than could be expected in view of the state of the art. The process is also suitable for stereoselective synthesis of the cis- and transcompounds of the formula (I), since on introduction of the double bond, essentially no isomerization of the corresponding starting compounds occurs.

If, for example, dichloromethane-phoshonic acid dimethyl ester and 3-formyl-2,2-dimethyl-cyclopropane-1-carboxylic acid iso-propyl ester are used as starting substances and potassium iso-propylate is used as the base, the reaction of these compounds can be outlined by the following equation:

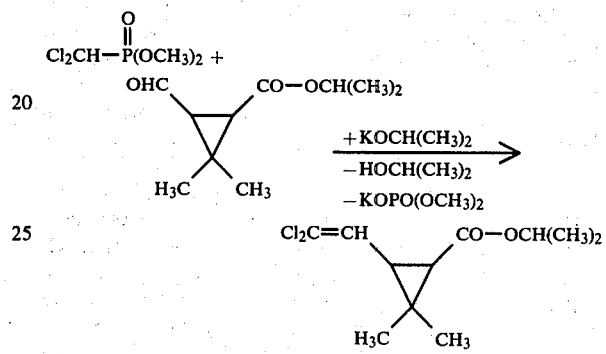

Formula (II) provides a definition of the 3-formyl-2,2-dimethyl-cyclopropane-1-carboxylic acid derivatives to be used as starting substances, Preferably, in this formula R represents hydrogen, sodium, potassium or straight-chain or branched alkyl with 1 to 4 carbon atoms.

Examples of the compounds (II) which may be mentioned are 3-formyl-2,2-dimethyl-cyclopropane-1-carboxylic acid and their sodium and potassium salts, 3-formyl-2,2-dimethylcyclopropane-1-carboxylic acid methyl ester, ethyl ester, n-propyl ester, iso-propyl ester, n-butyl ester, isobutyl ester, sec.-butyl ester and tert.-butyl ester.

Starting compounds of the formula (II) are known (see DE-OS (German Published Specification) No. 2,615,160; Tetrahedron Lett. 1978, 1847–1850; and U.S. Pat. No. 3,679,667).

Formula (III) provides a definition of the dichloromethane derivatives also to be used as starting compounds. Preferably, in this formula, $R^1$ and $R^2$ individually represent alkoxy with 1 to 4 carbon atoms or phenoxy, or $R^1$ and $R^2$ together represent straight-chain or branched alkanedioxy (alkylenedioxy) with 2 to 5 carbon atoms.

Examples of the compounds (III) which may be mentioned are dichloromethane-phosphonic acid dimethyl ester, diethyl ester and diphenyl ester.

Compounds of the formula (III) are known and can be prepared by processes which are in themselves known (see Synthesis 1975, 535–536; Tetrahedron Letters 1975 609–610; and ibid. 1975, 4409–4410).

Dichloromethane-phosphonic acid esters of the formula (III) are obtained, for example, by reacting dichloromethane-phosphonic acid dichloride (see British Patent Specification No. 707,961) with sodium salts or potassium salts of hydroxy compounds, for example with sodium methylate, ethylate, n- or isopropylate or n-, iso-, sec.- or tert.-butylate or potassium methylate, ethylate, n- or iso-propylate or n-, iso-, sec.- or tert.-butylate, if appropriate in the presence of a diluent, for example toluene, at a temperature between 0° and 50° C. To purify the products, they are distilled, if appropriate after filtration.

The process according to the invention is preferably carried out using a diluent. Possible diluents are virtually any of the inert organic solvents, especially aprotic polar solvents. These include ethers, for example glycol dimethyl ether, diglycol dimethyl ether, tetrahydrofuran and dioxane; carboxylic acid amides, for example dimethylformamide, dimethylacetamide and N-methyl-pyrrolidone; sulphoxides and sulphones, for example dimethylsulphoxide and tetramethylene sulphone; phosphoric acid amides, such as, hexamethylphosporic acid triamide; and nitriles, for example acetonitrile and propionitrile.

The bases customary in organochemical synthesis can be used in the process according to the invention. These bases include, as preferences, alkali metal hydroxides, for example sodium hydroxide and potassium hydoxide; alkali metal alcoholates, for example sodium methylate, potassium methylate, sodium ethylate, potassium ethylate, sodium iso-propylate, potassium isopropylate, sodium tert.-butylate and potassium tert.-butylate; alkali metal hydrides, for example sodium hydride and potassium hydride; alkali metal amides, for example sodium amide and potassium amide; alkyl-lithium compounds, for example butyl-lithium; and amines, for example diazabicyclononene and diazabicycloundecene.

Alcoholates are particularly preferred as the bases.

The reaction temperature is kept from about −50° to +50° C., preferably about −30° to +30° C. The process according to the invention is in general carried out under normal pressure.

1. to 1.5 mols, preferably 1 to 1.2 mols, of dichloromethane derivative of the formula (III) and 1 to 1.5 mols, preferably 1 to 1.2 mols, of base are preferably employed per mol of 3-formyl-2,2-dimethylcyclopropane-1-carboxylic acid derivative of the formula (II).

In a preferred embodiment of the process according to the invention, the starting substances of the formulae (II) and (III) in one of the abovementioned diluents are introduced into the reaction vessel at a temperature between −30° C. and +10° C. and a solution of a base in one of the abovementioned diluents is added dropwise. The reaction mixture is then allowed to come to room temperature and is subsequently stirred for some hours.

Working up is effected in the customary manner: the reaction mixture is poured into water and extracted with a water-immiscible solvent, for example methylene chloride. The extracts are washed with dilute sodium hydroxide solution and then with water dried and filtered. The solvent is stripped off from the filtrate and the product remaining as the residue is purified by vacuum distillation. It is characterized by its boiling point.

Since the 3-formyl-2,2-dimethyl-cyclopropane-1-carboxylic acid derivatives of the formula (II) employed as starting compounds and also the 3-(2,2-dichlorovinyl)-2,2-dimethyl-cyclopropane-1-carboxylic acid derivatives of the formula (I) to be prepared according to the invention each contain asymmetric carbon atoms, the compounds of the formulae (I) and (II) can have an appropriate number of stereoisomeric formulae.

The process according to the invention relates to the stereoselective preparation of compounds of the formula (I), which are obtained either in the form of the individual stereoisomers or as mixtures of stereoisomers.

The 2,2-dimethyl-3-(2,2-dichloro-vinyl)-cyclopropane-1-carboxylic acid derivatives to be prepared by the process according to the invention can be used as intermediate products for the preparation of insecticidally and acaricidally active pyrethroids (see DE-OS (German Published Specification) No. 2,326,077).

PREPARATIVE EXAMPLES

Example 1

(a)

266 g (2 mol) of aluminum chloride were added in portions to a mixture of 720 g (6 mol) of chloroform and 274 g (2 mol) of phosphorus trichloride.

The reaction mixture was then heated to the boiling point under reflux for 12 hours. The solvent was then stripped off in vacuo and the residue was taken up in 2 liters of methylene chloride. 440 ml of concentrated hydrochloric acid were added dropwise to this mixture at 0° C. and the mixture was subsequently stirred at this temperature for about two hours. The organic phase was separated off, dried over sodium sulphate and concentrated. The residue was subjected to fractional distillation. 258 g (64.5% of theory) of dichloromethane-phosphonic acid dichloride were obtained in the form of a colorless oil of boiling point 48°–50° C./1 mbar.

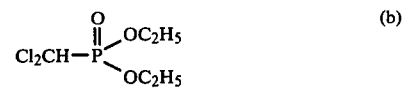
(b)

153.5 g (2.26 mol) of sodium ethylate in 800 ml of ethanol were added dropwise to a solution of 227.5 g (1.13 mol) of dichloromethane-phosphonic acid dichloride in 800 ml of toluene at 5°–10° C. The reaction mixture was subsequently stirred at 20° C. for five hours. It was then filtered, the filtrate was concentrated and the residue was subjected to fractional distillation. 195 g (78% of theory) of dichloromethane-phosphonic acid diethyl ester were obtained in the form of a colorless oil of boiling point 84° C./1 mbar.

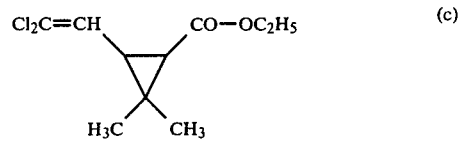
(c)

A suspension of 24.6 g (0.22 mol) of potassium tert.-butylate in 20 ml of dimethylformamide was added dropwise to a mixture of 48 g (0.22 mol) of dichloromethane-phosphonic acid diethyl ester and 34 g (0.2 mol) of 3-formyl-2,2-dimethyl-cyclopropane-1-carboxylic acid ethyl ester in 200 ml of tetrahydrofuran at −15° C. When the addition had ended, the reaction mixture was warmed to 20° C. and was stirred at this temperature for two hours.

The reaction mixture was then poured into 400 ml of water. The aqueous solution was extracted twice with 200 ml of methylene chloride each time. The combined organic extracts were washed once with 100 ml of 5% strength sodium hydroxide solution and twice with water, dried over sodium sulphate and then evaporated. The residue was subjected to fractional distillation. 42 g (88.6% of theory) of 3-(2,2-dichloro-vinyl)-2,2-dimethylcyclopropane-1-carboxylic acid ethyl ester were obtained in the form of a colorless oil of boiling point 80°–95° C./2 mbar.

Example 2

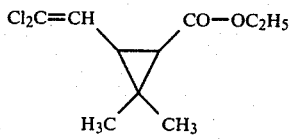

The reaction was carried out analogously to Example 1 with the same starting compounds, but instead of potassium tert.-butylate, sodium ethylate (15 g) was used as the base, and the reaction temperature at the start was kept at +10° C. 24.5 g (51.6% of theory) of 3-(2,2-dichloro-vinyl)-2,2-dimethyl-cyclopropane-1-carboxylic acid ethyl ester were obtained in the form of a colorless oil of boiling point 80°–95° C./2 mbar.

Example 3

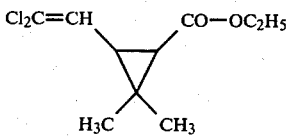

The reaction was carried out analogously to Example 1 with the same starting compounds, but instead of a solution of potassium tert.-butylate in dimethylformamide, a solution of the same base in 100 ml of tetrahydrofuran was used. 38 g (80% of theory) of 3-(2,2-dichlorovinyl)-2,2-dimethyl-cyclopropane-1-carboxylic acid ethyl ester were obtained in the form of a colorless oil of boiling point 80°–95° C./2 mbar.

EXAMPLE 4

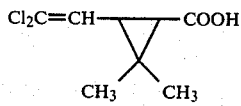

A suspension of 15 g sodium-methylate in 50 ml of dimethyl formamide was added dropwise to a mixture of 24 g (0,1 mol) of 3-formyl-2,2-dimethylcyclopropane-1-carboxylic acid and 22 g (0,1 mol) of dichloromethanephosphonic acid diethylester in 100 ml of tetrahydrofuran at −20° C.

The reaction mixture was stirred for 15 hours at room temperature (15° C.–25° C.), concentrated under reduced pressure and added to 200 ml water. The aqueous solution was extracted twice with diethylether cleared with charcoal and after filtration acidified with hydrochloric acid and then again extracted with methylene chloride. The methylene chloride phase was dried over sodium sulphate and then evaporated. The residue was 12 g finely crystallizing 3-(2,2-dichlorovinyl)-2,2-dimethyl-cyclopropanecarboxylic acid of a melting point of 80°–85° C.

It will be appreciated that the instant specification and examples are set forth by way of illustration and not limitation, and that various modifications and changes may be made without departing from the spirit and scope of the present invention.

We claim:

1. A process for the preparation of a 3-(2,2-dichlorovinyl)-2,2-dimethyl-cyclopropane-1-carboxylic acid or derivative of the formula

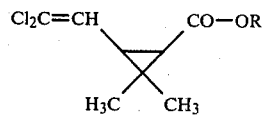

in which R is hydrogen, sodium, potassium or alkyl with 1 to 4 carbon atoms, comprising reacting a 3-formyl-2,2-dimethyl-cyclopropane-1-carboxylic acid or a derivative of the formula

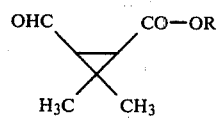

with a dichloromethane derivative of the formula

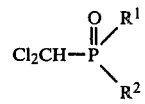

in which $R^1$ and $R^2$ each independently is alkyl, phenyl, alkoxy or phenoxy, or together are alkanediyl or alkanedioxy, in the presence of a base at a temperature between about −50° and +50° C.

2. A process according to claim 1, in which $R^1$ and $R^2$ each independently is alkoxy with 1 to 4 carbon atoms or phenoxy, or $R^1$ and $R^2$ together are alkanedioxy with 2 to 5 carbon atoms.

3. A process according to claim 1, wherein the reaction is effected between about −30° and +30° C.

4. A process according to claim 1, wherein the base is selected from alkali metal hydroxides, alkali metal alcoholates, alkali metal hydrides, alkali metal amides, alkyllithium compounds and amines.

5. A process according to claim 1, wherein the reaction is effected in an inert organic solvent.

6. A process according to claim 5, wherein the solvent is an aprotic polar solvent.

7. A process according to claim 1, wherein about 1 to 1.5 mols of the dichloromethane derivative and about 1 to 1.5 mols of the base are employed per mol of the cyclopropane-carboxylic acid or derivative.

8. A process according to claim 7, wherein about 1 to 1.2 mols of dichloromethane derivative and about 1 to 1.2 mols of the base are employed per mol of the cyclopropanecarboxylic acid or derivative.

9. A process according to claim 8, in which
   $R^1$ and $R^2$ each independently is alkoxy with 1 to 4 carbon atoms or phenoxy, or $R^1$ and $R^2$ together are alkanedioxy with 2 to 5 carbon atoms,
the reaction is effected between about −30° and +3° C. in an aprotic organic solvent, and the base is selected from alkali metal alcoholates.

* * * * *

UNITED STATES PATENT AND TRADEMARK OFFICE
CERTIFICATE OF CORRECTION

PATENT NO. : 4,296,241
DATED : Oct. 20, 1981
INVENTOR(S) : Hellmut Hoffmann et al It is certified that error appears in the above-identified patent and that said Letters Patent are hereby corrected as shown below:

Column 6, line 65    Delete "3" and insert --30--.

Signed and Sealed this

Twentieth Day of April 1982

[SEAL]

Attest:

GERALD J. MOSSINGHOFF

*Attesting Officer*    *Commissioner of Patents and Trademarks*